United States Patent [19]

Lape

[11] 4,062,651
[45] Dec. 13, 1977

[54] IGNITION MEANS IN A CHEMICAL ANALYZER FLAME PHOTOMETER

[75] Inventor: Larry J. Lape, Sugarland, Tex.

[73] Assignee: Hycel, Inc., Houston, Tex.

[21] Appl. No.: 725,236

[22] Filed: Sept. 21, 1976

[51] Int. Cl.² .................. G01N 33/16; G01N 21/58
[52] U.S. Cl. .................. 23/253 PC; 23/230 B;
    23/254 E; 356/87; 356/187
[58] Field of Search ............ 23/232 E, 232 R, 254 E,
    23/254 R, 255 E, 255 R, 230 PC, 230 B, 253
    PC; 73/23.1, 26; 356/187, 87

[56] References Cited
U.S. PATENT DOCUMENTS

| 2,811,891 | 11/1957 | Roddy, Jr. | 23/230 B |
| 3,330,960 | 7/1967 | Rich | 23/254 E |
| 3,489,498 | 1/1970 | Brody et al. | 23/254 E |
| 3,622,275 | 11/1971 | Staunton et al. | 23/230 PC |
| 3,689,225 | 9/1972 | White | 23/253 PC |

Primary Examiner—R.E. Serwin
Attorney, Agent, or Firm—Robert P. Cogan; Timothy L. Burgess

[57] ABSTRACT

In a flame photometer in a chemical analyzer, an electrical spark is used to ignite gas. An improved construction is provided in which an electrode is provided at the center of a nozzle screen, and the nozzle screen is utilized as a ground terminal. An improved electrode assembly facilitating ease of connection of a power source to the electrode is also provided.

6 Claims, 4 Drawing Figures

U.S. Patent  Dec. 13, 1977  4,062,651

IGNITION MEANS IN A CHEMICAL ANALYZER FLAME PHOTOMETER

BACKGROUND OF THE INVENTION

This invention relates to flame photometers in automatic chemical analyzers and more particularly to improved ignition electrode assemblies therein.

Flame photometers of the type contemplated are primarily utilized for measuring sodium and potassium levels in human serum. A gas flame is provided, such as from a propane source, and ignited at a screen at an end of a gas nozzle. The screen is important in that it shapes the flame so that appropriate wavelength filters and photocells may be positioned with respect to the flame for reading the intensity at a selected wavelength of radiation emitted by samples introduced into the flame. Normally a flame diluent is provided and vapors thereof are put into an air path passing along the flame, and colors produced thereby are read by the photocells. A suitable flame diluent is a solution of lithium carbonate in water. Lithium produces a good background wavelength, i.e. it will screen out undesired background light and does not produce a wavelength in the same area of interest as sodium and potassium. Lithium is also a good selection since lithium will not be found in human serum except perhaps in the cases of persons taking certain psychedelic drugs.

Conventionally, igniter means are provided adjacent an upper screen for igniting the gas at the initiation of operation. Igniter means may commonly comprise, for example, an electrode mounted on or adjacent the screen and a second electrode mounted at a point remote therefrom. An important constraint on mounting a remote electrode is that it must be mounted outside of the path of the flame so as not to interfere therewith but must not be mounted too far from the screen. Mounting an electrode too far from the screen requires a very large voltage to break down and ionize gas in order to produce a spark. Also, some electrode arrangements which require a relatively large amount of gas flow before ignition present the potential for a flare-up upon the ignition. Another desirable characteristic is that the electrodes be of the type whose operation is not impeded under adverse conditions of flame burning. More specifically, if a flame burns too leanly, various components chemicals in the vapor passing over through the flame will deposit on the electrode. Where the electrode consists of an exposed point rather than an exposed larger surface, the electrode may be covered with deposits and require either greater voltage for operation or perhaps even cease operation. Another desirable characteristic is that the electrodes be easily assembled. Further, should an electrode require a replacement it is desirable to have a system in which minimum disruption to the flame photometer system is required.

SUMMARY OF THE INVENTION

It is therefore an object of the present invention to provide a flame photometer for chemical analysis in which a simplified construction is provided.

It is a further object to provide a flame photometer of the type described in which electrodes are positioned for non-interference with flame shaping and in which said electrodes have a large surface area compared to point electrodes.

It is also a specific object of the present invention to provide a flame photometer in which a gas nozzle screen comprises one electrode.

It is a further object of the present invention to provide a flame photometer of the type described in which a detachable connection to one electrode is easily made and in which ease of the assembly is provided.

Briefly stated, in accordance with the present invention, there is provided a flame photometer in a chemical analyzer in which a gas nozzle is provided in a chimney for a flow of vapor containing samples to be analyzed. A flame screen is provided at an upper end of the nozzle. For igniting gas flowing through the nozzle, an electrode projecting through the center of the flame screen is provided comprising a first electrode, and the flame screen itself is another electrode. Further, an assembly housing the first electrode is provided for facilitating electrical connection thereto and mechanical mounting to the gas nozzle assembly.

BRIEF DESCRIPTION OF THE DRAWINGS

The means by which the foregoing object and features of invention are achieved are pointed out with particularity in the claims forming the concluding portion of the specification. The invention, both as to its organization, and manner of operation, may be further understood by reference to the following description taken in connection with the following drawings.

Of the drawings.

DESCRIPTION OF THE PREFERRED EMBODIMENT

Figure 1:
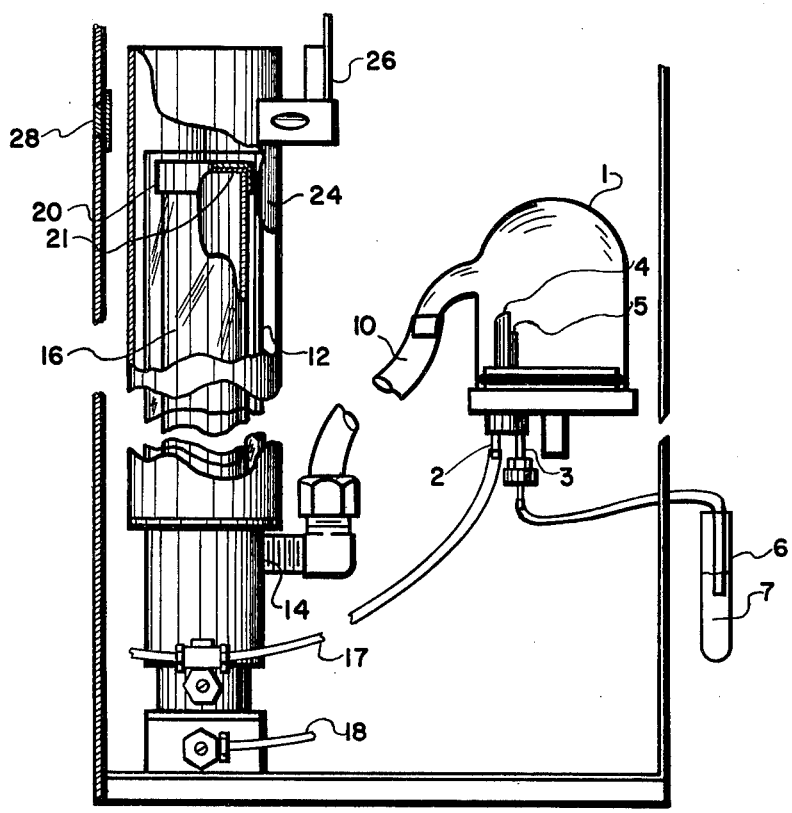
FIG. 1 is an illustration of a flame photometer chemical analyzer of the type contemplated for use in the present invention.

Referring to FIG. 1, there is illustrated a fluid circuit for a chemical analyzer flame photometer. A mixing chamber 1 has an air inlet 2 and a sample inlet 3. Air coming into a nozzle 4 withdraws sample by the Venturi effect from a sample nozzle 5 to provide atomized sample in the chamber 1. The sample to the inlet 3 may be withdrawn from a reaction container 6 having a sample 7 therein consisting, for example, of diluted serum. The chamber 1 is connected by an air line 10 to the base of a chimney 12 having an air inlet 14. Housed inside the chimney 12 is a vertically disposed nozzle 16 having an air inlet 17 and a gas inlet 18. A retaining ring 20 holds a screen 21 to the top of the nozzle 16.

An outer housing 24 substantially concentric with the chimney 12 holds photocells in filters in a unit 26 for connection to conventional processing circuitry (not shown). The unit 26 is positioned for viewing a predetermined portion of the flame projected from the nozzle 16 at the screen 21. A viewing window 28 may be formed in the outer housing 14 in registration with the photocell and filter unit 26 for an operator's viewing of the flame. Atomized sample is drawn into the flame, and the intensity at predetermined wavelengths as measured by the filter and photocell unit 26 indicates the amount of sodium and potassium in the serum. In order to provide for this measurement, of course, the flame must be ignited. The means for doing this are shown in further detail in FIG. 2 which is a partial view of the nozzle 16 and the assembly including the screen 21.

Figure 2:
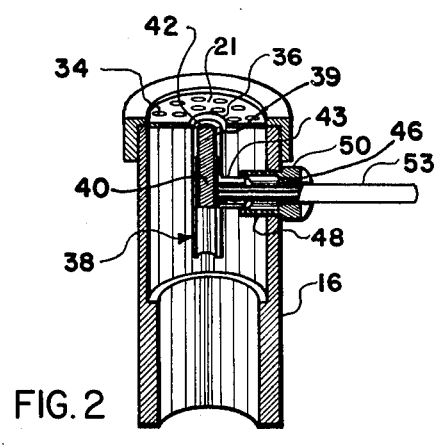
FIG. 2 is a detailed view, partially broken away of the photometer nozzle assembly incorporating the present invention.

In FIG. 2, the retaining ring 20 is removed for simplicity of illustration, and the screen 21 is shown sitting on top of the nozzle 16. The screen 21 includes a plurality of holes 34 which are positioned for shaping a flame to be viewed by the photocell unit 26 (FIG. 1). The spacing inside of the holes is of great importance, and is done in well-known manner. At the center of the screen 21, a circular aperture 36 is formed through which an igniter electrode assembly 38 has an upper end projecting. The igniter assembly 38 comprises a vertical cylindrical portion 39 open at an upper end and closed at a lower end and having a conductive rod 40 fused therein and projecting from the upper end therefrom. The conductive rod 40 projects from an upper end of the housing 38 to define a first electrode 42. In the present embodiment, an alternating source of potential is provided. Alternatively, in conjunction with the use of a direct current potential, the electrode 42 would comprise a positive electrode. In accordance with the present invention, the nozzle 16, and consequently the screen 21, is connected to what is commonly called chassis ground. More rigorously stated, the screen 21 is connected to a level of reference potential, in the present embodiment ground potential. The conducting rod 40 may be any number of conductive materials. Preferably, the electrode 42 consists of a tungsten rod 40 with is two percent thoriated.

In order to make electrical connection to the electrode assembly 38, an aperture 46 is provided in registration with a cylindrical projection 43 of the assembly which communicates with the interior of the cylindrical portion 39 38. The aperture 46 receives mechanical connecting means comprising a cylindrical member 48 having an outer radial flange 50. The cylindrical portion 48 extends through the aperture 46 and has an outer diameter substantially equal to the inner diameter of the cylindrical projection 43. The cylindrical member 48 is preferably constructed of a material such as polytetrafluoroethylene (PTFE). The cylindrical number 48 receives conductor means 53 such as a wire press fit therein to make connection to the conducting rod 40.

Figure 3:
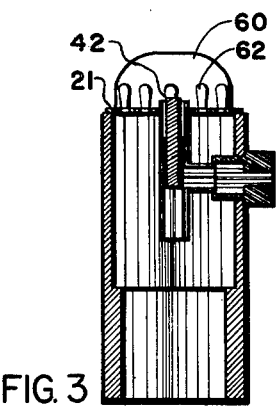
FIG. 3 is a detailed cross sectional view of an electrode assembly of the present invention.

Referring to FIG. 3, operation of the present invention is illustrated. When gas flows through the screen 21 and is ignited, a flame cone 60 is formed, which is the resulting of individual component flames 62 at each hole 24 in the screen 21. It should be noted that electrode assembly 38 positioned at the center thereof has no adverse effect on flame shaping. The electrode 42 is out of the way of the flame cone 60.

In operation, gas flow is started and a circuit (FIG. 4) is closed to form a spark through a spark gap from the electrode 42 to the screen 21. Voltage requirements are minimized due to the short distance therebetween. Further, both the electrode 42 and screen 21 have large surface areas compared to ordinary point electrodes. Therefore, should chemicals be deposited from samples on portions of either the electrode 42 or screen 21, operation will not be impeded. A large amount of surface area is still available for completion of a circuit. It should also be noted that positioning of the electrode 42 at the center of the screen 21 takes full advantage of desirable characteristics for flame shaping. A proper shape flame cone 60 is provided, by positioning the electrode 42 at the center of the screen 21. Space is utilized efficiently where it would not be desired to have a flame hole 34 anyway. The provision of too many holes 34 in the screen 21 results in provision of too hot a flame cone 60 for proper measurements to be made.

Figure 4:
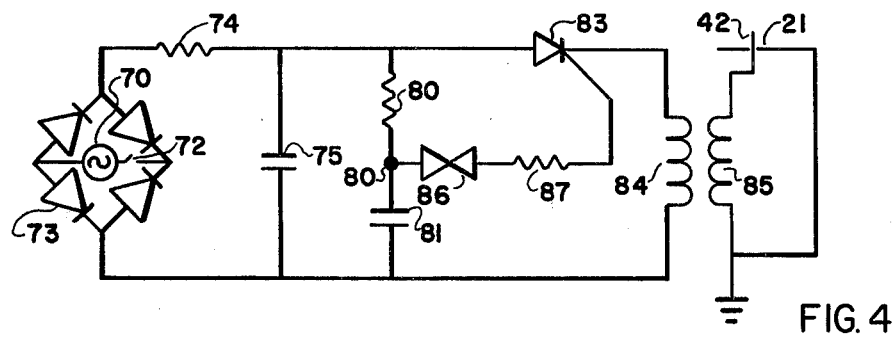
FIG. 4 is a schematic illustration of the system of the present invention.

Circuitry for the present operation is disclosed in FIG. 4. An alternating current source 70 is provided connected in series to a "flame on" switch 72 for connecting the source 70 to a full wave rectifier 73. A resistor 74 and capacitor 75 are connected across the full wave rectifier 73 for charging the capacitor 75. A switching circuit 79 is connected across the capacitor 75 for periodically discharging the capacitor 75. A resistor 80 and capacitor 81 are connected the series across the capacitor 75. Unilateral controlled switching means in the form of an SCR 83 are connected in series with a spark coil primary winding 84 also across the capacitor 75. Bilateral threshold sensitive breakdown means in the form of a Diac 86 are connected in series with a resistor 87 between the gate of the SCR 83 and a terminal 88 intermediate the resistor 80 and capacitor 81. The primary winding 84 is inductively coupled to a secondary winding 85 having one and thereof connected to a ground and through ground connected to the screen 21 and having a second terminal connected to the electrode 42.

When the switch 72 is closed, the capacitor 75 charges. Since the source 70 is a conventional 60 Hz. source, breakdown voltage of the Diac 86 is periodically exceeded, whereby the SCR 83 is triggered. When the SCR 83 is triggered, the capacitor 75 discharges therethrough, and voltage across the primary winding 84 and induces the voltage appearing across the secondary winding 85. The turns ratio of winding 85 is selected to provide a high voltage, i.e. sufficient to break down air and gas over the short distance between the electrode 42 and screen 21, for providing an ignition spark. In this manner the flame is lit, and then the switch 72 may be opened.

What is thus provided is a flame photometer ignition system in a chemical analyzer in which interference of ignition means with the flame shaping is minimized and in which efficient construction is provided.

What is claimed as new and desired to be secured by Letters Patent of the United States is:

1. In a flame photometer in a chemical analyzer comprising a nozzle, gas source, and atomized sample source for interaction with a flame and means for measuring wavelengths of samples in the flame, the improvement comprising: an electrically conductive screen mounted to said nozzle for forming a flame, means connecting said screen to a source of reference potential, an aperture formed in said screen, an electrode assembly comprising an electrode housed in insulating means, and means mounting said electrode assembly for projection through said aperture, whereby a spark gap is defined between said screen and said electrode.

2. The improvement according to claim 1 wherein said electrode assembly comprises an electrode rod mounted in a first portion of said electrode asembly, said first portion having in communication therewith an open ended projection therefrom, an aperture in said nozzle in registration with said projection, and mechanical connecting means projecting through said aperture and receiving said projection for mounting said electrode assembly to said nozzle.

3. The improvement according to claim 2 wherein said electrode assembly comprises a tungsten rod fused in a glass sleeve.

4. The improvement according to claim 3 further comprising conductor means for connecting said electrode to a source of ignition potential, said conductor means extending through said mechanical connecting means and through said projection and being press fit against said electrode.

5. The improvement according to claim 3 wherein said aperture in said screen is formed at the center thereof.

6. The improvement according to claim 2 wherein said electrode assembly comprises a conductive rod mounted in an insulating sleeve.

* * * * *